US009907807B2

(12) United States Patent
Evers et al.

(10) Patent No.: US 9,907,807 B2
(45) Date of Patent: Mar. 6, 2018

(54) TOPICAL PHARMACEUTICAL COMPOSITIONS

(71) Applicant: Almirall, S.A., Barcelona (ES)

(72) Inventors: Fritjof Evers, Reinbek (DE); Henning Mallwitz, Buchholz/N. (DE); Ricarda Wessel, Neumarkt (DE); Christoph Willers, Hamburg (DE)

(73) Assignee: ALMIRALL, S.A., Barcelona (ES)

( * ) Notice: Subject to any disclaimer, the term of this patent is extended or adjusted under 35 U.S.C. 154(b) by 0 days.

(21) Appl. No.: 14/883,898

(22) Filed: Oct. 15, 2015

(65) Prior Publication Data

US 2016/0038512 A1    Feb. 11, 2016

Related U.S. Application Data

(63) Continuation of application No. 13/699,333, filed as application No. PCT/EP2011/002369 on May 13, 2011, now abandoned.

(60) Provisional application No. 61/365,050, filed on Jul. 16, 2010.

(30) Foreign Application Priority Data

May 26, 2010  (EP) .................................... 10382146

(51) Int. Cl.
| | | |
|---|---|---|
| *A61K 31/58* | (2006.01) | |
| *A61K 9/00* | (2006.01) | |
| *A61K 9/06* | (2006.01) | |
| *A61K 9/107* | (2006.01) | |
| *A61K 47/06* | (2006.01) | |
| *A61K 47/10* | (2017.01) | |

(52) U.S. Cl.
CPC ............ *A61K 31/58* (2013.01); *A61K 9/0014* (2013.01); *A61K 9/06* (2013.01); *A61K 9/107* (2013.01); *A61K 47/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 4,775,529 A | 10/1988 | Sequeira et al. | |
| 4,808,610 A | 2/1989 | Munayyer et al. | |
| 5,696,105 A | 12/1997 | Hackler | |
| 2010/0029602 A1 | 2/2010 | Arkin et al. | |
| 2014/0200203 A1 | 7/2014 | Evers et al. | |
| 2016/0038512 A1 | 2/2016 | Evers et al. | |

FOREIGN PATENT DOCUMENTS

| | | | |
|---|---|---|---|
| DE | 102006034883 A1 | 1/2008 | |
| EP | 0 735 885 A1 | 10/1996 | |
| EP | 1 886 686 A1 | 2/2008 | |
| EP | 2 394 653 A1 | 12/2011 | |
| EP | 2 575 822 B1 | 4/2013 | |
| ES | 2 221 928 | 1/2005 | |
| WO | WO 91/08733 | 6/1991 | |
| WO | WO 99/18971 | 4/1999 | |
| WO | WO 2003/097070 A1 | 11/2003 | |
| WO | WO 2004/105686 A2 | 12/2004 | |
| WO | WO 2008/126076 A2 | 10/2006 | |
| WO | WO 2008126076 A2 * | 10/2008 | ........... A61K 9/0014 |
| WO | WO 2011/147536 A2 | 12/2011 | |
| WO | WO 2011/147536 A3 | 12/2011 | |

OTHER PUBLICATIONS

Dumas, Kenneth et al., "The Psoriasis Bio-Assay for Topical Corticosteroid Activity," Acta Dermatovener (Stockholm), vol. 52, pp. 43-48 (1972).
English language Derwent Abstract of EP 1 886 686 A1.
English language translation of EP 1 866 686 A1.
Espacenet English language abstract of ES 2 221 928.
International Search Report and Written Opinion for PCT International Application No. PCT/EP2011/002369, dated Apr. 4, 2012.
McKenzie, A.W., et al., "Method for comparing percutaneous absorption of steriods," Arch. Dermatol., vol. 86, pp. 608-610 (1962).
Wikipedia entry for "2-Methyl-2,4-pentanediol" (updated: Apr. 17, 2014; retrieved: Jul. 8, 2014) http://en.wikipedia.org/wiki/2-Methyl-2,4-pentanediol (6 pages).
Canadian Search Report dated Feb. 21, 2017, for Canadian Patent Application No. 2,794,553 (1 page).
Examination Report dated Dec. 7, 2017, for Indian Patent Application No. 9831/CHENP/2012, 6 pages.

* cited by examiner

*Primary Examiner* — Jared D Barsky
(74) *Attorney, Agent, or Firm* — Finnegan, Henderson, Farabow, Garrett & Dunner LLP

(57) ABSTRACT

Topical pharmaceutical compositions are described comprising, based on the total weight of the composition: a) 0.01 to 0.2 wt. % of mometasone furoate, b) 5 to 18 wt. % of hexylene glycol, c) 20 to 40 wt. % of water, and d) 25 to 70 wt. % of an oil phase. Said compositions are stable and can be safely and easily applied over large surface areas of the skin in an acceptable way by the general patient population for the treatment or prevention of psoriasis, atopic dermatitis (atopic eczema) and other skin disorders or diseases.

6 Claims, No Drawings

TOPICAL PHARMACEUTICAL COMPOSITIONS

This is a continuation of application Ser. No. 13/699,333, filed Nov. 21, 2012, which is a national stage filing under 35 U.S.C. § 371 of international Application No. PCT/EP2011/002369 filed May 13, 2011, which claims priority to European Patent Application No. 10382146.8, filed May 26, 2010, and U.S. Provisional Application No. 61/365,050 filed Jul. 16, 2010, all of which are incorporated herein by reference.

FIELD OF THE INVENTION

The present invention relates to topical pharmaceutical compositions comprising mometasone furoate. Said compositions are stable and can be safely and easily applied over large surface areas of the skin in an acceptable way by the general patient population. The invention further relates to a process for the preparation of said compositions and to methods of treatment by administering the compositions.

BACKGROUND OF THE INVENTION

Topical corticosteroids, as a class, demonstrate anti-inflammatory, anti-pruritic and vasoconstrictive actions. They are generally used to relieve the redness, skin edema (swelling), itching, crusting, flaking, blistering, cracking, oozing and discomfort of psoriasis, atopic dermatitis (atopic eczema) and other pathologies of the skin like contact dermatitis, seborrheic dermatitis, xerotic eczema, discoid eczema, venous eczema, dermatitis herpetiformis, neurodermatitis or autoeczematization.

Commercially, topical corticosteroid products are available as ointments, creams, solutions, foams and lotions. The Food and Drug Administration (FDA), Center for Drug Evaluation and Research (CDER) Data Standards Manual, Dosage Form (version 08) defines ointment as "a semisolid dosage form, usually containing less than 20% water and volatiles and more than 50% hydrocarbons, waxes, or polyols as the vehicle, which is generally for external application to the skin or mucous membranes"; cream as "an emulsion, semisolid dosage form, usually containing more than 20% water and volatiles and/or less than 50% hydrocarbons, waxes, or polyols as the vehicle, which is generally for external application to the skin or mucous membranes"; and lotion as "an emulsion, liquid dosage form, which is generally for external application to the skin".

Due to their physico-chemical properties lotions are more pleasant to be used (cosmetically accepted) to the end-user than ointments or creams, e.g. lotions are easily applied than ointments or creams and are typically used for the treatment of large body areas, to hair-covered skin and on the hairy scalp.

While the mechanisms of the anti-inflammatory effects are unclear, there appears to be a correlation between the therapeutic effects of corticosteroids and their vasoconstrictive potencies. Vasoconstrictor assays have been commonly used to compare and predict the relative therapeutic potencies of topically applied corticosteroids (McKenzie A. W., Stoughton R. B.: Method for comparing percutaneous absorption of steroids. Arch Dermatol 1962; 86: 608-610)

Mometasone furoate is a corticosteroid commonly used in the treatment of inflammatory skin disorders, allergic rhinitis (such as hay fever), and asthma. Mometasone furoate is a fine white to off-white powder that is insoluble in water, slightly soluble in octanol, and moderately soluble in ethyl alcohol. The exceptionally poor solubility of mometasone furoate is a limitation for the development of topical pharmaceutical compositions.

Different solvents have been used in order to develop topical pharmaceutical compositions containing mometasone furoate, either containing said mometasone furoate partially dissolved and partially suspended or containing the drug totally dissolved due to the presence of solubilizing agents.

Thus, U.S. Pat. No. 4,775,529 describes topical pharmaceutical compositions containing corticosteroids (including mometasone furoate) in a hydro-alcoholic base comprising a) 15-50 wt. % of propylene glycol, b) 20-40 wt. % of isopropyl alcohol, c) 20-60 wt. % of water, d) 0.1-3.0 wt. % of a thickening agent and e) a buffer to adjust the pH between 3.0 to 6.0. Other topical mometasone furoate/propylene glycol pharmaceutical compositions are disclosed in WO 9108733, WO2004105686 and WO2008126076.

On the other side, U.S. Pat. No. 4,808,610 discloses topical pharmaceutical compositions comprising a) 0.01-0.25% of mometasone furoate, b) 5-20% of hexylene glycol, c) 1.0-5.0% of water, d) 2.0-10.0% of white wax, e) 40-70% of white petrolatum and other ingredients. U.S. Pat. No. 4,808,610 indicates that when mometasone furoate is partially dissolved and partially suspended in propylene glycol based cream formulations, the resulting formulations do not possess the necessary efficacy; and when mometasone furoate is completely dissolved in oleyl alcohol/propylene glycol based cream formulations, the resulting formulations not only lack the required activity but also are irritant in a rabbit dermal test. Additionally, according to U.S. Pat. No. 4,808,610, formulations containing drug solubilizing agents may result in poor activity.

Finally, EP 1886686 describes topical pharmaceutical compositions comprising a) 0.01-0.2 wt. % of mometasone furoate, b) 10-90 wt. % of water and c) a combination of at least an aromatic alcohol and at least a solvent selected from two different groups, and e) optionally further additives. According to EP 1886686 the combination of the aromatic alcohol and the solvent increases the solubility of mometasone furoate avoiding its precipitation even in the case of increasing the water content.

Surprisingly, it has been found that topical pharmaceutical compositions comprising mometasone furoate suspended in hexylene glycol based formulations (i.e. topical pharmaceutical compositions comprising solid particles of mometasone furoate dispersed in hexylene glycol based formulations) are stable, exhibit an efficacy comparable to mometasone furoate compositions available in the market and, due to its physico-chemical properties, are easily applied to the skin (easy to spread on the skin), in particular to hair-covered skin, absorb rapidly, not being irritant to the skin and, as a result, being more pleasant to use to the general patient population.

SUMMARY OF THE INVENTION

It has now surprisingly been found that topical pharmaceutical compositions comprising, based on the total weight of the composition:
a) 0.01 to 0.2 wt. % of mometasone furoate,
b) 5 to 18 wt. % of hexylene glycol,
c) 20 to 40 wt. % of water, and
d) 25 to 70 wt. % of an oil phase,
are stable and exhibit a comparable efficacy to mometasone furoate compositions available in the market although having a higher water content and containing the mometasone furoate suspended (dispersed) in the composition and not dissolved. Furthermore, due to its physico-chemical properties, said topical pharmaceutical compositions are easily applied to the skin (easy to spread on the skin), in particular to hair-covered skin, absorb rapidly, not being irritant to the skin and, as a result, being more pleasant to use to the general patient population.

Additionally, patients treated with the topical pharmaceutical compositions of the invention presented better skin hydration values and skin adsorption times than patients treated with mometasone furoate compositions available in the market.

The invention further relates to a composition as defined above for use in the treatment or prevention of psoriasis, atopic dermatitis (atopic eczema) and other skin disorders or diseases.

The invention further relates to the use of a composition as defined above for the manufacture of a medicament for the treatment or prevention of psoriasis, atopic dermatitis (atopic eczema) and other skin disorders or diseases.

The invention further relates to a method for treating a subject afflicted with psoriasis, atopic dermatitis (atopic eczema) and other skin disorders or diseases, which comprises applying to the affected area of skin of said subject an effective amount of a topical pharmaceutical composition as defined above.

DETAILED DESCRIPTION OF THE INVENTION

Mometasone Furoate

Mometasone furoate [9α,21-dichloro-11β,17-dihydroxy-16α-methylpregna-1,4-diene-3,20-dione 17-(2-furoate)] is a corticosteroid having the empirical formula $C_{27}H_{30}Cl_2O_6$, and a molecular weight of 521.4 g/mol.

According to the invention, preferably anhydrous mometasone furoate is used. Anhydrous mometasone furoate is mometasone furoate that lacks an associated water molecule. Anhydrous mometasone furoate can be distinguished from mometasone furoate monohydrate, which is a hydrated form of mometasone furoate that has a molecular formula of $C_{27}H_{30}Cl_2O_6 \cdot H_2O$.

Hexylene Glycol

Hexylene glycol (2-Methyl-2,4-Pentanediol) is a clear, colourless, viscous liquid which absorbs moisture when exposed to moist air. It is miscible with water, alcohol, ether, chloroform, acetone, and many other organic solvents. Hexylene glycol has the empirical formula $C_6H_{14}O_2$, and a molecular weight of 118.2 g/mol.

The Aqueous Liquid Pharmaceutical Compositions

The present invention provides topical pharmaceutical compositions comprising, based on the total weight of the composition:
a) 0.01 to 0.2 wt. % of mometasone furoate,
b) 5 to 18 wt. % of hexylene glycol,
c) 20 to 40 wt. % of water, and
d) 25 to 70 wt. % of an oil phase.

In the topical pharmaceutical compositions according to the invention the amount of a) mometasone furoate, is preferably in the range of 0.05 to 0.15 wt. %, more preferably 0.08 to 0.12 wt. % based on the total weight of the composition.

The amount of compound b) hexylene glycol, is preferably in the range of 7 to 15 wt. %, more preferably 8 to 13 wt. % based on the total weight of the composition.

The amount of compound c) water, is preferably in the range of 25 to 40 wt. %, more preferably 25 to 35 wt. %, even more preferably 26 to 34 wt. % based on the total weight of the composition.

Preferably, the topical pharmaceutical compositions according to the invention further comprise, based on the total weight of the composition, d) 25 to 70 wt. %, preferably 30 to 65 wt. %, more preferably 35 to 45 wt. %, of an oil phase.

According to the invention, an oil is a substance that is in a viscous liquid state ("oily") at room temperature or slightly warmer, and is both hydrophobic (immiscible with water) and lipophilic (miscible with other oils). Suitable oil phases according to the invention are petroleum hydrocarbons (mineral oils, paraffins and waxes), animal and vegetable fats and oils, fatty acids, fatty alcohols, natural waxes, silicones and polyols other than hexylene glycol, or mixtures thereof.

Suitable petroleum hydrocarbons, i.e. mineral oils, paraffins and waxes from petroleum according to the present invention are: hard paraffin, liquid paraffin (Liquid Petrolatum or Paraffinum Liquidum), light liquid paraffin (Light Liquid Petrolatum or Paraffinum Perliquidium), white soft paraffin (White Petrolatum), yellow soft paraffin (Yellow Petrolatum), macrocrystalline paraffin waxes (which are mixtures which consist mainly of saturated $C_{18}$-$C_{30}$ hydrocarbons and smaller amounts of iso-alkanes and cycloalkanes with a molecular weight comprised between 250 and 450 g/mol and, although they are solids at room temperature, they have low melting points, usually comprised between 40° C. and 60° C.), microcrystalline paraffines waxes (which consist of $C_{40}$-$C_{55}$ compounds which contain, in addition to normal hydrocarbons, large amounts of iso-alkanes and naphtenes with long alkyl side-chains, the iso-alkanes forming microcrystals, the microcrystalline paraffines waxes having mean molecular weights comprised between 500 and 800 g/mol, being solids at room temperature, and having melting points comprised between 60° C. and 90° C.), or mixtures thereof. Preferred petroleum hydrocarbons are hard paraffin, liquid paraffin, light liquid paraffin, white soft paraffin or mixture thereof, being particularly preferred liquid paraffin, white soft paraffin or mixtures thereof.

Suitable animal or vegetable fats and oils according to the present invention are esters of linear and/or branched, saturated and/or unsaturated alkanecarboxylic acids with a chain length of 1 up to 30 carbon atoms and linear and/or branched, saturated and/or unsaturated alcohols with a chain length of 1 up to 30 carbon atoms; or are esters of aromatic carboxylic acids and linear and/or branched, saturated and/or unsaturated alcohols with a chain length of 1 up to 30 carbon atoms.

These oils can be advantageously selected from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl laurate, 2-ethylhexyl palmitate, 2-ethylhexyl cocoate, 2-hexyldecyl stearate, 2-ethylhexyl isostearate, 2-octyldodecyl palmitate, cetyl palmitate, oleyl oleate, oleyl erucate, erucyl oleate, erucyl erucate, as well as synthetic, semisynthetic and natural mixtures of such esters, such as jojoba oil (a natural mixture of esters of monounsaturated monocarboxylic acids with a $C_{18}$-$C_{24}$ chain with also monounsaturated monoalcohols and with a long $C_{18}$-$C_{24}$ chain).

Other suitable oils of the type of esters of saturated alkanecarboxylic acids and alcohols are fatty acid methyl esters, preferably $C_6$-$C_{24}$ fatty acid methyl esters from animal and vegetable fats and oils such as cotton, safflower, coconut, rapeseed, linseed, palm, palm kernel, sunflower, olein, olive, olive pomace, castor oil, tallow, soy, tall oil, etc, possibly totally or partially hydrogenated, as well as purified or synthetic fatty acids such as caproic acid, caprylic acid, capric acid, lauric acid, myristic acid, palmitic acid (cetylic acid), palmitoleic acid, stearic acid, isostearic acid, 2-ethylhexanoic acid, oleic acid, ricinoleic acid, elaidic acid, petroselinic acid, linoleic acid, linolenic acid, arachidic acid, gadoleic acid, behenic acid and erucic acid, or mixtures thereof.

Other suitable animal or vegetable fats and oils according to the present invention are fatty acid triglycerides, specifically triglycerin esters of linear and/or branched, saturated and/or unsaturated alkanecarboxylic acids with a chain length of 6 up to 24 carbon atoms, preferably of 10 up to 18 carbon atoms. The fatty acids esterifying the different positions of glycerin can be different, giving rise to a large amount of possible combinations, including positional combinations. The position of the different fatty acids in natural triglycerides is not random, but rather it depends on the origin of the fat. The triglycerides more simple are those constituted by a sole fatty acid.

Fatty acid triglycerides can be advantageously chosen, for example, from the group consisting of synthetic, semi-synthetic and natural oils, as for example, animal fats and oils such as cow tallow, pig lard, bone oil, aquatic animal fats and oils (fish, such as herring, cod or sardine; cetaceans; etc.); and vegetable fats and oils such as avocado oil, almond oil, hazelnut oil, babassu palm oil, borage oil, peanut oil, canola oil, hemp oil, milk thistle oil, safflower oil, chufa oil, coconut oil, rapeseed oil, black cumin oil, wheat germ oil, sunflower oil, linseed oil, macadamia nut oil, corn oil, walnut oil, olive oil and its by-products such as olive pomace oil, palm oil and its fractions such as palm olein and palm stearin, evening primrose oil, rosehip oil, castor oil, rice bran oil, apricot kernel oil, cottonseed oil, pumpkinseed oil, palm kernel oil and its fractions such as palm kernel olein and palm kernel stearin, grape seed oil, sesame oil, soy oil, cocoa butter, shea butter and the like.

Particularly preferred are vegetable fats and oils as described above.

Suitable fatty acids according to the present invention are $C_6$-$C_{24}$ fatty acids from vegetable and animal fats and oils, such as those previously described, such as cotton, safflower, coconut, rapeseed, linseed, palm, palm kernel, sunflower, olein, olive, olive pomace, castor oil, tallow, soy, tall oil, etc, possibly totally or partially hydrogenated, as well as purified or synthetic fatty acids such as caproic acid, caprylic acid, capric acid, lauric acid, myristic acid, palmitic (cetylic) acid, palmitoleic acid, stearic acid, isostearic acid, 2-ethylhexanoic acid, oleic acid, ricinoleic acid, elaidic acid, petroselinic acid, linoleic acid, linolenic acid, arachidic acid, gadoleic acid, behenic acid and erucic acid, or or technical grade mixtures thereof. Fatty acids of the lauric, myristic, palmitic, palmitoleic, stearic, isostearic, 2-ethylhexanoic, oleic, ricinoleic, behenic type, or mixtures thereof are preferred, in particular, those from vegetable origin.

Suitable fatty alcohols according to the present invention are $C_6$-$C_{24}$ fatty alcohols from vegetable and animal fats and oils such as those previously described, such as cotton, safflower, coconut, rapeseed, linseed, palm, palm kernel, sunflower, olein, olive, olive pomace, castor oil, tallow, soy, tall oil, etc, possibly totally or partially hydrogenated, as well as purified or synthetic fatty alcohols such as caproyl alcohol, capryl alcohol, capric alcohol, lauryl alcohol, myristyl alcohol, palmytil (cetyl) alcohol, palmitoyl alcohol, stearyl alcohol, isostearyl alcohol, 2-octyldodecanol, 2-ethylhexanoyl alcohol, oleyl alcohol, ricinoleyl alcohol, elaidyl alcohol, petroselinic alcohol, linoleyl alcohol, linolenyl alcohol, arachidyl alcohol, gadoleyl alcohol, behenyl alcohol and erucyl alcohol, or technical grade mixtures thereof such as cetostearyl alcohol. Fatty alcohols of the lauryl, myristyl, palmityl, palmitoleyl, stearyl, isostearyl 2-ethylhexanoyl, oleyl, ricinoleyl and behenyl type, or technical grade mixtures thereof such as cetostearyl alcohol are preferred, in particular, those from vegetable origin.

Suitable natural waxes according to the present invention are the candelilla wax, carnauba wax, Japan wax, esparto wax, cork wax, guaruma wax, rice wax, sugar cane wax, ouricury wax, montan wax, beeswax, shellac wax, espermaceti, wool lanolin (wax), uropygial fat wax, ceresin waxes, peat waxes, ozokerite, as well as chemically modified waxes (hard waxes) for example, montan wax esters, waxes obtained by the Fischer-Tropsch process, hydrogenated jojoba waxes and synthetic waxes.

Silicones suitable according to the present invention are cyclic and/or linear silicones, which can be found as monomers generally characterized by structural elements such as:

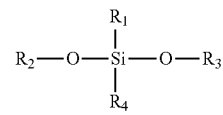

where the silicon atoms can be substituted by alkyl or aryl radicals equal or different, represented here generally by $R_1$-$R_4$ groups.

Linear silicones with siloxane units suitable according to the present invention are generally characterized by structural elements such as:

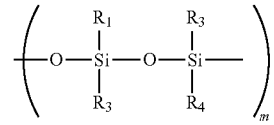

where the silicon atoms can be substituted by alkyl or aryl radicals equal or different, are represented here in general by $R_1$-$R_4$ groups (meaning the number of different radicals is not necessarily limited to 4), m can take values from 2 to 200,000.

Cyclic silicones suitable according to the present invention are generally characterized by structural elements such as:

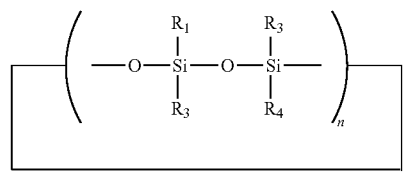

where the silicon atoms can be substituted by alkyl or aryl radicals equal or different, represented here generally by $R_1$-$R_4$ groups (meaning the number of different radicals is not necessarily limited to 4), n can take values of 3/2 to 20.

Fractional values of n indicate that it may be odd numbers of siloxane groups present in the ring.

Specific examples include a cyclic methyl siloxane having the formula $[(CH_3)_2SiO]_x$ in which x is 3-6, or short chain linear methyl siloxanes having the formula $((CH_3)_2SiO[(CH_3)_2SiO]_ySi(CH_3)_3$ in which y is 0-5.

Some suitable cyclic methyl siloxanes are hexamethylcyclotrisiloxanes (D3), a solid with a boiling point of 134° C. and the formula $[(Me_2)SiO]_3$; octamethylcyclotetrasiloxane (D4) with a boiling point of 176° C., a viscosity of 2.3 mm$^2$/s, and the formula $[(Me_2)SiO]_4$; decamethylcyclopentasiloxane (D5) (cyclomethicone) with a boiling point of 210° C., a viscosity of 3.87 mm$^2$/s, and the formula $[(Me_2)SiO]_5$; and dodecamethylcyclohexasiloxane (D6) with a boiling point of 245° C., a viscosity of 6.62 mm$^2$/s and the formula $[(Me_2)SiO]_6$.

Some suitable short linear methyl siloxane are hexamethyldisiloxane (MM) with a boiling point of 100° C., viscosity of 0-65 mm$^2$/s, and formula $Me_3SiOMe_3$; octamethyltrisiloxane (MDM) with a boiling point of 152° C., viscosity of 1.04 mm$^2$/s, and formula $Me_3SiOMe_2SiOSiMe_3$; decamethyltetrasiloxane (MD2M) with a boiling point of 194° C., viscosity of 1.53 mm$^2$/s, and formula $Me_3SiO(MeSiO)_2SiMe_3$; dodecamethylpentasiloxane (MD3M) with a boiling point of 229° C., viscosity of 2.06 mm$^2$/s, and formula $Me_3SiO(Me_2SiO)_3SiMe_3$; tetradecamethylhexasiloxane (MD4M) with a boiling point of 245° C., viscosity of 2.63 mm$^2$/s, and formula $Me_3SiO(Me_2SiO)_4SiMe_3$; and hexadecamethylheptasiloxane (MD5M) with a boiling point of 270° C., viscosity of 3.24 mm$^2$/s, and formula $Me_3SiO(Me_2SiO)_5SiMe_3$.

Furthermore, long chain linear siloxanes such as phenyltrimethicone, bis(phenylpropyl)dimethicone, dimethicone, dimethiconol, cyclomethicone (octametilciclotetrasiloxane), hexamethylcyclotrisiloxane, poly(dimethylsiloxane), cetyldimethicone and behenoxy dimethicone are also included.

In addition, mixtures of cyclomethicone and isotridecyl isononanoate and of cyclomethicone and 2-ethylhexyl isostearate are also suitable silicones according to the invention.

Suitable polyols other than hexylene glycol according to the present invention are preferably water-soluble polyols such as polyhydric alcohols with two or more hydroxyl groups in their molecule. Specific examples can include ethylene glycol, propylene glycol, 1,3-butylene glycol, 1,4-butylene glycol, dipropylene glycol, polyethylene glycol with average molecular weights by weight ranging between 100 and 1000, glucose, fructose, galactose, mannose, ribose, erythrose, maltose, maltitose, maltotriose, sucrose, xylitol, sorbitol, threitol, erythritol, glycerol, polyglycerol and starch alcohols. Preferred polyols other than hexylene glycol are ethylene glycol, propylene glycol, 1,3-butylene glycol, 1,4-butylene glycol, dipropylene glycol, polyethylene glycol with average molecular weights by weight ranging between 100 and 1000, glycerol, polyglycerol, and mixtures thereof.

Preferred topical pharmaceutical compositions of the invention comprise, based on the total weight of the composition:
a) 0.01 to 0.2 wt. %, preferably 0.05 to 0.15 wt. %, more preferably 0.08 to 0.12 wt. % of mometasone furoate,
b) 5 to 18 wt. %, preferably 7 to 15 wt. %, more preferably 8 to 13 wt %. of hexylene glycol,
c) 20 to 40 wt. %, preferably 25 to 35 wt. %, more preferably 26 to 34 wt. % of water, and
d) 25 to 70 wt. %, preferably 30 to 65 wt. %, more preferably 35 to 45 wt. % of an oil phase.

In a preferred embodiment, the topical pharmaceutical compositions of the invention comprise, based on the total weight of the composition:
a) 0.05 to 0.15 wt. %, preferably 0.08 to 0.12 wt. % of mometasone furoate,
b) 7 to 15 wt. %, preferably 8 to 13 wt. % of hexylene glycol,
c) 25 to 35 wt. %, preferably 26 to 34 wt. % of water,
d1) 32 to 50 wt. %, preferably 35 to 48 wt. % of petroleum hydrocarbons,
d2) 5 to 12 wt. %, preferably 7 to 10 wt. % of $C_6$-$C_{24}$ fatty alcohols, and
d3) 0.1 to 5 wt %, preferably 0.5 to 3 wt. % of polyols other than hexylene glycol.

In a further preferred embodiment, the topical pharmaceutical compositions of the invention comprise, based on the total weight of the composition:
a) 0.08 to 0.12 wt. % of mometasone furoate,
b) 8 to 13 wt. % of hexylene glycol,
c) 26 to 34 wt. % of water,
d1) 35 to 48 wt. % of petroleum hydrocarbons selected from liquid paraffin, white soft paraffin or mixtures thereof,
d2) 7 to 10 wt. % of $C_6$-$C_{24}$ fatty alcohols selected from lauryl alcohol, miristyl alcohol, palmityl alcohol, stearyl alcohol, oleyl alcohol or mixtures thereof, and
d3) 0.5 to 3 wt. % of glycerol.

The pH value of the topical pharmaceutical compositions according to the invention is typically within the acceptable range for topical administration, and is preferably in the range of 3.0 to 6.0, more preferably in the range of 3.5 to 5.0.

The viscosity of the topical pharmaceutical compositions according to the invention is typically in the range of 2,000 to 15,000 mPa·s, preferably in the range of 2,500 to 10,000 mPa·s, more preferably in the range of 3,000 to 7,000 mPa·s measured at 20° C. using a DIN-Rotations Rheometer (Paar Physica); Measuring System Z 3 DIN; D=57 1/s.

The topical pharmaceutical compositions according to the invention may optionally further comprise other well-known pharmaceutically and/or cosmetically acceptable additives, such as, e.g. anti-irritants, antioxidants, buffering agents (pH adjusting agents), chelating agents, emollients, penetration enhancing agents, preservative agents, solubilizing agents, thickening agents, wetting agents, and the like, or mixtures thereof.

Examples of suitable anti-irritants are aloe vera, chamomile, alpha-bisabolol, cola nitida extract, green tea extract, tea tree oil, licoric extract, batyl alcohol (α-octadecyl glyceryl ether), selachyl alcohol (α-9-octadecenyl glyceryl ether), chimyl alcohol (α-hexadecyl glyceryl ether), panthenol, allantoin, caffeine or other xanthines, glycyrrhizic acid and derivatives thereof, and mixtures thereof.

Antioxidants used can be any antioxidants which are suitable or customary for cosmetic and/or dermatological applications. Suitable antioxidants are advantageously selected from the group consisting of amino acids (for example glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very small tolerated doses (e.g. pmol to μmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), and coniferylbenzoate of benzoin, rutinic acid and derivatives thereof, ferulic acid and derivatives thereof, butylated hydroxytoluene, butylated hydroxyanisole, nordihydroguaiac resin acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenium methionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Any pharmaceutically acceptable buffering agents to adjust the pH of the aqueous liquid pharmaceutical compositions according to the invention to be within the acceptable range for topical administration, preferably in the range of 3.0 to 6.0, more preferably in the range of 3.5 to 5, can be used. For example the inclusion in the composition of a pharmaceutically acceptable acid such as acetic, citric, fumaric, phosphoric, hydrochloric, lactic or nitric acids or the like, or a mixture thereof. It will also be understood that certain compositions of the invention can have a pH in the desired range without inclusion of a pH adjusting agent specifically for that purpose. Typically, however, an acidic buffer system is present in the composition to achieve the desired pH. An acidic buffer system comprises an acidulant and a buffering agent. Suitable acidulants will be known to those of skill in the art and illustratively include acetic, citric, fumaric, hydrochloric, phosphoric, lactic and nitric acids and the like, and mixtures thereof. Suitable buffering agents will likewise be known to those of skill in the art and illustratively include potassium metaphosphate, potassium phosphate, sodium phosphate, sodium acetate, sodium citrate and the like, and mixtures thereof.

Suitable emollients, which can be used in the composition of the present invention include, for example, dodecane, squalane, cholesterol, isohexadecane, isononyl isononanoate, PPG Ethers, petrolatum, lanolin, safflower oil, castor oil, coconut oil, cottonseed oil, palm kernel oil, palm oil, peanut oil, soybean oil, polyol carboxylic acid esters, derivatives thereof, and the like, and combinations thereof.

Examples of suitable penetration enhancing agents can include, e.g., dimethylsulfoxide (DMSO), N-methyl pyrrolidine, dimethyl formamide (DMF), allantoin, urazole, N,N-dimethylacetamide (DMA), decylmethylsulfoxide, polyethylene glycol monolaurate, propylene glycol, propylene glycol monolaurate, glycerol monolaurate, lecithin, the 1-substituted azacycloheptan-2-ones, particularly 1-n-dodecylcyclazacycloheptan-2-one, alcohols, glycerin, hyaluronic acid, transcutol, and the like, and combinations thereof. Certain oil components (e.g., certain vegetable oils such as, e.g., safflower oil, cottonseed oil and corn oil) also can exhibit penetration enhancing properties.

Examples of suitable preservatives to prevent microbial contamination are alkylparabens, particularly methylparaben, propylparaben and butylparaben; sodium benzoate; butylated hydroxy toluene; butylated hydroxyanisole; ethylenediamine tetraacetic acid; chlorobutanol; benzyl alcohol; phenylethylalcohol; dehydroacetic acid; sorbic acid; potassium sorbate; benzalkonium chloride; benzethonium chloride; and mixtures thereof. The amount of preservative generally utilized will vary depending upon the preservative selected.

Examples of solubilizing agents are, for example, nonionic surfactants from at least one of the following groups: products of the addition of 1 to 30 moles of ethylene oxide and/or 0 to 5 moles of propylene oxide onto linear $C_8$-$C_{22}$ fatty alcohols, $C_{12}$-$C_{22}$ fatty acids and alkyl phenols containing 8 to 15 carbons in the alkyl group; alkyl and/or alkenyl oligoglycosides containing 8 to 22 carbons in the alkyl group and ethoxylated analogs thereof; addition products of 1 to 15 moles of ethylene oxide with castor oil and/or hydrogenated castor oil; addition products of 15 to 60 moles of ethylene oxide with castor oil and/or hydrogenated castor oil; partial esters of glycerol and/or sorbitan with unsaturated or saturated, linear or branched fatty acids containing 12 to 22 carbons and/or hydroxycarboxylic acids containing 3 to 18 carbon atoms and addition products thereof with 1 to 30 moles of ethylene oxide; mixtures of alkoxylated glycerides and alkoxylated glycerine, partial esters of polyglycerol (average degree of selfcondensation 2 to 8), polyethylene glycol (weight average molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbons and/or hydroxycarboxylic acids containing 3 to 18 carbons and addition products thereof with 1 to 30 moles of ethylene oxide; mixed esters of pentaerythritol, fatty acids, citric acid and fatty alcohol and/or mixed esters of fatty acids containing 6 to 22 carbons, methyl glucose and polyols, preferably glycerol or polyglycerol; mono-, di- and trialkyl phosphates and mono-, di- and/or tri-PEG-alkyl phosphates and salts thereof; block copolymers, for example Polyethyleneglycol-30 Dipolyhydroxystearate; polymer emulsifiers; polyalkylene glycols and alkyl glyceryl ethers. Particularly preferred solubilizing agents are products of the addition of 1 to 30 moles of ethylene oxide and/or 0 to 5 moles of propylene oxide onto linear $C_8$-$C_{22}$ fatty alcohols such as lauryl, myristyl, cetyl (palmityl), stearyl, oleyl, and ricinoleyl alcohols, or technical grade mixtures thereof such as cetostearyl alcohol or palmitoleyl alcohol.

A thickening agent or viscosity-enhancing agent can be included to generally thicken the liquid pharmaceutical compositions. While any suitable thickening agent can be included in the compositions of the present invention, a preferred thickening agent, when used, includes one or more of acacia, alginic acid bentonite, carbomer, carboxymethylcellulose calcium or sodium, cetostearyl alcohol, methyl cellulose, ethylcellulose, glycerin, gelatin guar gum, hydroxyethylcellulose, hydroxypropylcellulose, hydroxypropylmethylcellulose, maltodextrin, polyvinyl alcohol, povidone, propylene carbonate, propylene glycol alginate, sodium alginate, sodium starch glycolate, starch tragacanth, and xanthan gum, and any combination thereof. More preferred thickening agents are glycerin, hydroxypropylmethylcellulose, and xanthan gum, and any combination thereof.

Examples of wetting agents (chemical substances that increase the spreading and penetrating properties of a liquid by lowering its surface tension) include one or more cationic surfactants, such as benzalkonium chloride; non-ionic surfactants such as polyoxyethylene and polyoxypropylene block copolymers; polyoxyethylene fatty acid glycerides and oils (such as polyoxyethylene (6) caprylic/capric mono- and diglycerides), polyoxyethylene (40) hydrogenated castor oil; polyoxyethylene sorbitan esters, such as polysorbate 20 and polysorbate 80; propylene glycol fatty acid esters, such as propylene glycol laureate; glyceryl fatty acid esters, such as glyceryl monostearate; sorbitan esters, such as sorbitan monolaurate, sorbitan monooleate, sorbitan monopalmitate and sorbitan monostearate; glyceryl fatty acid esters, for example glyceryl monostearate; anionic surfactants such as sodium lauryl sulphate, sodium lauryl ether sulphate; or fatty acids and salts thereof, such as oleic acid, sodium oleate and triethanolamine oleate.

The invention further relates to a topical pharmaceutical composition as defined above for use in the treatment or prevention of psoriasis, atopic dermatitis (atopic eczema) and other skin disorders or diseases, such as contact dermatitis, seborrheic dermatitis, xerotic eczema, dyshidrosis, discoid eczema, venous eczema, dermatitis herpetiformis, neurodermatitis or autoeczematization.

The topical pharmaceutical composition of the invention is preferably formulated in the form of a cream.

The invention further relates to the use of a topical pharmaceutical composition as defined above for the manufacture of a medicament for the treatment or prevention of psoriasis, atopic dermatitis (atopic eczema) and other skin disorders or diseases, such as contact dermatitis, seborrheic dermatitis, xerotic eczema, dyshidrosis, discoid eczema, venous eczema, dermatitis herpetiformis, neurodermatitis or autoeczematization.

The invention further relates to a method for treating a subject afflicted with psoriasis, atopic dermatitis (atopic eczema) and other skin disorders or diseases, such as contact dermatitis, seborrheic dermatitis, xerotic eczema, dyshidrosis, discoid eczema, venous eczema, dermatitis herpetiformis, neurodermatitis or autoeczematization, which comprises applying to the affected area of skin of said subject an effective amount of a topical pharmaceutical composition as defined above.

The method of using the topical pharmaceutical composition of the invention is by applying it to completely cover the affected area, forming an occlusive barrier. The usual frequency of application is once daily, although adequate maintenance therapy for some patients may be achieved with less frequent application.

The following examples are given in order to provide a person skilled in the art with a sufficiently clear and complete explanation of the present invention, but should not be considered as limiting of the essential aspects of its subject, as set out in the preceding portions of this description.

EXAMPLES

Example 1

A cream according to the invention was prepared having the composition indicated in Table 1 (wt. % based on the total weight of the composition)

TABLE 1

Mometasone furoate cream

| Ingredients | wt. % |
|---|---|
| Mometasone furoate | 0.1 |
| Liquid Paraffin | 17.5 |
| White Soft Paraffin | 26.5 |
| Cetostearyl Alcohol[1] | 7.2 |
| Macrogol Cetostearyl Ether[2] | 2.8 |
| Cetyl Alcohol | 1.0 |
| Hexylene Glycol | 10.0 |
| Glycerol | 1.0 |
| Xanthan Gum | 0.1 |
| Purified Water | up to 100% |
| pH adjusted to 3.5-4.5 | |

[1]Emulsifying Cetostearyl Alcohol Type A
[2]Having 20-30 units of ethylene oxide per molecule Said cream was prepared in the following manner:
1) Oil phase: white soft paraffin, liquid paraffin, cetostearyl alcohol, macrogol cetostearyl ether and cetyl alcohol were added to a main vessel equipped with anchor stirrer and homogeniser. The ingredients were heated to 70° C. and melted while stirring until obtaining an homogenous mixture.
2) Xanthan gum phase: Xanthan gum was pre-dispersed in hexylene glycol.
3) Water phase: About 90 wt. % of the total amount of water was added to a stainless steel container and heated to 70° C. A pH adjuster was added to the water and dissolved while stirring. The xanthan gum phase (step 2) was added while homogenizing.
4) Combination: The hot aqueous phase of step (3) was transferred to the main vessel while stirring and subsequent homogenizing.
5) The combined phases were cooled down to 25° C. while stirring.
6) Mometasone furoate was pre-dispersed in glycerol. This dispersion was diluted with the remaining purified water and then transferred to the emulsion while homogenizing.

Example 2

The viscosity of the cream of Example 1 was measured at 20° C. using a DIN-Rotations Rheometer (Paar Physica); Measuring System Z 3 DIN; D=57 1/s.

Additionally, the viscosity of a commercially available mometasone cream such as ECURAL® Fettcreme 0.1% of Essex Pharma GmbH (Comparative Example 1) using the same measuring conditions.

According to the product information, each gram of ECURAL® Fettcreme 0.1% contains: 1 mg mometasone furoate in a cream base of hexylene glycol; phosphoric acid; propylene glycol stearate; stearyl alcohol and ceteareth-20; titanium dioxide; aluminum starch octenylsuccinate; white wax; white petrolatum; and purified water. The water content of ECURAL® Fettcreme is about 3 to 5 wt. %.

The results are indicated in Table 2.

TABLE 2

| Viscosity values | |
|---|---|
| Example 1 | Comparative Example 1 |
| aprox. 5,000 mPa · s | aprox. 20,000 mPa · s |

From the experimental results it can be concluded that the cream of Example 1 (according to the invention) can be more easily applied than the cream of Comparative Example 1 (commercially available)

Example 3

A vasoconstrictor assay measuring skin blanching (assay described by Mckenzie and Stoughton, Arch. Dermatol., 86, 608-610 (1962)) was used to determine the bioequivalence of the cream of Example 1 (according to the invention) to ECURAL® Fettcreme 0.1% (Comparative Example 1)

Study population: 30 Subjects with healthy skin in the area of the test fields, demonstrating adequate vasoconstriction to corticosteroids, aged 18 years or older, were investigated.

Test performance: Single topical non-occlusive application to test fields located on the volar surface of the forearms. Skin colour in the treated and untreated test fields was measured using chromametry. In addition, the degree of vasoconstriction was clinically assessed compared to the untreated test fields.

Efficacy: Under the conditions in the present vasoconstrictive assay the topical bioavailability of the cream of Example 1 was shown by a strong blanching effect. The strong blanching effect of the cream of Example 1 was comparable to the effect of Comparative Example 1. Similar mean AUCs were noted for the cream of Example 1 (according to the invention) and for Comparative Example 1 (commercially available). The topical bioavailability of the active formulations was shown by chromametric measurement and clinical assessment.

Example 4

A psoriasis bio-assay for topical corticosteroid activity—psoriasis plaque test (assay described by Dumas and Scholtz, Acta Dermatovener (Stockh), 52, 43-48 (1972)) was also used to determine the bioequivalence of the cream of Example 1 (according to the invention) to ECURAL Cream 0.1% (Comparative Example 1).

Twenty-two male or female subjects were enrolled. The test fields on psoriatic skin were descaled and treated occlusively over a study period of 12 days.

The cream of Example 1 demonstrated a strong positive effect in the treatment of psoriasis. The antipsoriatic effect of the cream of Example 1 was comparable to the effect seen for Comparative Example 1 on the basis of the sonographic measurements and global clinical assessment. No clinical improvement was seen for the active ingredient-free vehicle.

The invention claimed is:

1. A topical pharmaceutical composition comprising, based on the total weight of the composition:
    a) 0.08 to 0.12 wt. % of mometasone furoate,
    b) 8 to 13 wt. % of hexylene glycol,
    c) 26 to 34 wt. % of water, and
    d1) 35 to 48 wt. % of petroleum hydrocarbons chosen from liquid paraffin, white soft paraffin and mixtures thereof,
    d2) 7 to 10 wt. % of $C_6$-$C_{24}$ fatty alcohols chosen from lauryl alcohol, miristyl alcohol, palmityl alcohol, stearyl alcohol, oleyl alcohol and mixtures thereof, and
    d3) 0.5 to 3 wt. % of glycerol,
    wherein the mometasone furoate is suspended in the composition.

2. The composition according to claim 1, wherein the composition further comprises anti-irritants agents, antioxidants agents, buffering agents, chelating agents, emollients, penetration enhancing agents, preservative agents, solubilizing agents, thickening agents, wetting agents or mixtures thereof.

3. The composition according to claim 1, wherein the composition has a pH value in the range of 3.0 to 6.0.

4. The composition according to claim 1, wherein the composition is formulated in the form of a cream.

5. A method for treating a subject afflicted with psoriasis or atopic dermatitis, comprising applying to the affected area of skin of said subject an effective amount of the composition of claim 1.

6. The composition according to claim 1, wherein the total amount of a) mometasone furoate is 0.1 wt. %, based on the total weight of the composition.

* * * * *